United States Patent [19]

Hitzman

[11] E Re. 30,272

[45] Reissued May 13, 1980

[54] RECOVERY OF CELLULAR PROTEIN PRODUCTS FROM MICROBIOLOGICAL SYNTHESIS MASSES

[75] Inventor: Donald O. Hitzman, Bartlesville, Okla.

[73] Assignee: Phillips Petroleum Company, Bartlesville, Ohio

[21] Appl. No.: 755,762

[22] Filed: Dec. 30, 1976

Related U.S. Patent Documents

Reissue of:

[64] Patent No.: 3,958,038
Issued: May 18, 1976
Appl. No.: 418,915
Filed: Nov. 26, 1973

[51] Int. Cl.[2] ..... A23J 1/00

[52] U.S. Cl. ..... 426/656; 435/68

[58] Field of Search ..... 426/656, 657, 61; 195/4, 59, 75, 96, 29; 260/112 R, 112 G, 119; 210/42, 45, 54

[56] References Cited

U.S. PATENT DOCUMENTS

| | | | |
|---|---|---|---|
| 2,251,334 | 8/1941 | Hall | 426/656 X |
| 3,681,283 | 8/1972 | Yueh | 210/54 |
| 3,778,514 | 12/1973 | Olson | 426/61 |
| 3,833,552 | 9/1974 | Akin | 260/112 R |
| 4,105,804 | 8/1978 | Terui et al. | 426/656 |

OTHER PUBLICATIONS

Orten, James M. et al., Biochemistry Eighth Edition, 1970, p. 89.

Jacobs, *The Chemistry and Technology of Food and Food Products*, vol. II, (1951), Interscience Publishers, Inc., New York, pp. 843, 893.

*Primary Examiner*—Robert A. Yoncoskie
*Assistant Examiner*—E. M. Kepplinger

[57] ABSTRACT

Cellular protein products are recovered from microbiologically produced masses by incorporation therewith of a protein material suitable as a food which acts as a flocculant.

8 Claims, No Drawings

RECOVERY OF CELLULAR PROTEIN PRODUCTS FROM MICROBIOLOGICAL SYNTHESIS MASSES

Matter enclosed in heavy brackets [ ] appears in the original patent but forms no part of this reissue specification; matter printed in italics indicates the additions made by reissue.

This invention relates to the recovery of cellular protein products from microbiological processes, e.g. fermentation, biosynthesis of petroproteins, bacteria growth, etc. More specifically, the invention relates to a method of harvesting the cells produced in such processes. In one of its aspects, the invention relates to recovery of such cells as herein described at ambient temperature.

In one of its concepts the invention provides a process for recovery of cellular protein products from microbiologically produced masses containing the same by adding to such masses a food supplement capable of acting as a flocculating agent. In another of its concepts the invention provides a balanced, synthetically produced food comprising cellular protein product referred to herein supplemented by materials capable of acting as a food and capable of acting as a flocculating agent.

I have discovered that certain protein supplements can be used successfully to flocculate the cells, produced as earlier stated, thus providing a product which can then be separated readily from the liquid growth medium. Such separation can be accomplished, for example, by filtration, centrifugation or any other process which is capable of separating the flocculated cells which are intimately associated with said flocculating agent. Thus I have discovered, for example, that certain protein supplements which are capable of functioning very well as flocculants and which therefore are now particularly preferred and recommended are skim milk and gluten.

Nutritionists believe that all amino acids must be present at the site of protein synthesis in animals (including humans) in proper proportions for this synthesis to occur. A deficiency of any essential amino acid, say at 50% of its requirement would have some effect regardless of which essential amino acid was lacking. Further, if any essential amino acid were not included in the diet, protein synthesis would essentially stop. The effect would be comparable to feeding no protein at all. While this theory is not exactly true, deficiencies of some amino acids, notably threonine, isoleucine, methionine, and cystine, can essentially arrest or prevent protein production in an animal when excluded from its diet.

The nutritive quality of a protein is dependent on its content of essential amino acids, i.e., those which cannot be synthesized by the animal (including human). It has been pointed out that in order to maintain nitrogen equilibrium about 4% of the total energy consumed by an adult human must be in the form of protein containing a balanced mixture of amino acids. The term "animal protein" is often used synonymously with "high quality" protein but the quality of the protein depends on the amino acid composition or amino acid profile. The single cell proteins provided in the art by various fermentation processes, including the one used as an example herein are "animal proteins." Depending on the type of cells, feed stock, etc., the amino acid profile of these "unicellular animal proteins" will be different and a complementary protein source may be desirable.

In known processes, cells are recovered from the growth media by adjusting the pH to a low value, i.e., about 3, by heating the cell broth to coagulate the cells and/or addition of a chemical, non-nutritive flocculating agent. These recovery treatments have a deleterious effect on the proteins and other nutrients in the cells and growth medium so that a process which can recover cells at ambient temperatures and/or higher pH than 3 is desirable.

It is an object of this invention to recover cellular protein products from microbiologically produced masses containing the same. It is also an object of this invention to produce a balanced food stuff or product capable of acting as a food for animals. Another object of this invention is to improve the recovery of proteinaceous products while avoiding the deleterious effects of large pH range change adjustments. It is still a further object of the invention to provide such a process in which no heat needs to be used, thus avoiding deleterious effects of heat.

According to the present invention there is provided a process for the recovery of cellular protein products from masses containing the same, produced by microbiological processes, which comprises adding to the mass to flocculate the same a material capable of acting as a food supplement and as the essential flocculant to be used.

It will be understood by those skilled in the art in possession of this disclosure having studied the same that as long as the food supplement is present and causing flocculation other aids to flocculation can be used.

Also, according to the invention there is produced a product which can be tailored to have varying compositions and to have variation in the amino acid balance therein.

The recovery process of this invention operates at ambient temperature and does not require a large range change pH adjustment. Consequentially, the nutrient liquid can be reused. Valuable products therein can be recovered without risking injury by heat or change in pH to vitamins, nucleic acids, enzymes. The advantages are set out below:

1. No heat is required which permits obtaining a product not altered or degraded by heat. Heat has the advantage of yielding a sterile product.

2. The pH does not have to be as low as formerly which also prevents product deterioration and saves acid and neutralization costs.

3. The edible protein is all recovered with the cells which adds to the product's nutritional and economic value.

4. By correct choice of edible protein, limiting amino acids in both products complement each other leading to a premium product.

5. Addition of a protein low in nucleic acids helps to reduce the nucleic acid content of the total product.

6. Acceptability, fabrication, and texturing of the product is improved by such blends.

The various cell protein products, of the invention have, of course, varying compositions and there is considerable variation in the amino acid balance. One of the important concepts of this invention lies in the selection of the flocculant in nature and amount such that it will supply one or more amino acids in which the culture is particularly deficient and incidentally also will supply some valuable minerals and/or other food constituents such as carbohydrates; so that the final product, composed of single cell protein and food supplement flocculant, will be a balanced food. This is achieved without the necessary addition of known chemical flocculants such as alum or sodium silicate which add nothing to the nutritive value of the product and may even in some cases not only dilute but destroy some of the benefits otherwise obtainable.

The inventive concept is illustrated in the example below in which the amino acid profile of two flocculants, skim milk powder and gluten and two single cell proteins are given. The first section compares grams of amino acid/100 grams product. The selected flocculants also contain non-proteins. Thus a more convenient comparison is based on the protein content only. This is provided in the second section in which proteins are compared. The relative amounts of a specific amino acid in grams/100 grams protein material clearly show up the differences in amino acid content of the flocculants and cells. The analyses of the flocculants were made on the actual materials used in the experiments detailed later.

IMPROVEMENT OF PROTEIN QUALITY OF SINGLE CELL PROTEINS (SCP) BY USE OF FLOCCUANTS WITH COMPLEMENTARY NUTRITIONAL PROPERTIES

ESSENTIAL AMINO ACID CONTENT OF FLOCCULANTS AND SCP PRODUCTS

| Essential Amino Acid | Skimmed Milk Powder | Gluten | Bacterial SCP | Yeast SCP | Skimmed Milk Powder | Gluten | Bacterial SCP | Yeast SCP |
|---|---|---|---|---|---|---|---|---|
| Leucine | 3.63 | 5.52 | 5.51 | 4.47 | 10.63 | 7.16 | 7.30 | 8.13 |
| Isoleucine | 1.88 | 2.68 | 2.99 | 2.87 | 5.50 | 3.48 | 3.96 | 5.22 |
| Lysine | 2.77 | 1.29 | 3.94 | 4.02 | 8.10 | 1.67 | 5.22 | 7.31 |
| Methionine | 0.69 | 1.15 | 1.26 | 0.68 | 2.01 | 1.50 | 1.67 | 1.24 |
| Cystine | 0.09 | 1.04 | 0.30 | 0.47 | 0.26 | 1.35 | 0.40 | 0.85 |
| Threonine | 1.33 | 1.58 | 2.71 | 2.83 | 3.80 | 2.05 | 3.59 | 5.51 |
| Phenylalanine | 1.92 | 3.64 | 2.34 | 2.92 | 5.60 | 4.72 | 3.10 | 5.31 |
| Tyrosine | 1.64 | 2.69 | 2.65 | 2.64 | 4.80 | 3.48 | 3.51 | 4.80 |
| Tryptophane | —[1] | — | 0.50 | 1.10 | — | — | 0.66 | 2.00 |
| Valine | 2.34 | 2.79 | 3.84 | 3.44 | 6.80 | 3.61 | 5.09 | 6.25 |

[1]Tryptophane was not analyzed for in these flocculants.

Cystine is an essential amino acid which is often present in proteins in insufficient quantities. Gluten contains three times as much of this amino acid as bacterial SCP. If enrichment of cystine is required, then gluten can be selected as flocculant in sufficient quantities to raise the cystine content even though a smaller amount might be sufficient to effect the flocculation. The methionine content of yeast SCP can be improved by a skimmed milk powder flocculant. Note that cystine is one of the essential amino acids, the absence of which will inhibit protein synthesis completely (v.s.) in an animal. The above examples are illustrative of the concept of complementary flocculants.

Usually 0.2–25% by weight, based on total weight of cells and growth medium of a flocculant will be used, preferably 1–15 wt. %. However, if the flocculant has some particular food value which is to be incorporated in the final product, more of the flocculant can be used. In other words, in the separation step of the single cell protein product using a nutrient flocculant, a blending concept is also incorporated to provide exactly the nutritional balance desired. Of course, this implies that two or more flocculants or even a non-flocculant can be used to achieve such balance.

The flocculants listed below were tested in recovery processes of single cell proteins.

Example

A bacterial culture was prepared by fermentation. In a 14 liter capacity fermenter was placed 6 liters of nutrient medium number 1. Sufficient ammonia was added to adjust the pH to 6.8 and 60 cc of methanol were added as carbon source. The medium was inoculated with Pseudomonas methanica which has been assigned the number NRRLB-3449 by the Northern Regional Research & Development Division, Peoria, Illinois. Fermentation was continued for 48 hours and the methanol concentration and pH were maintained by periodic addition of methanol and $NH_4OH$.

Nutrient Medium Number 1

All Ingredients per liter of aqueous solution

| | |
|---|---|
| 85% $H_3PO_4$ | 2.0 milliliter |
| KCl | 1.0 g |
| $MgSO_4 . 7H_2O$ | 1.5 g |
| $CaCl_2 . 2H_2O$ | 0.2 g |
| NaCl | 0.1 g |
| Trace minerals | 5.0 ml |
| Trace Mineral Solution g/l | |
| $CuSO_4 . 5H_2O$ | 0.06 |
| KI | 0.08 |
| $MnSO_4 . H_2O$ | 0.30 |
| $H_3BO_3$ | 0.02 |
| $ZnSO_4 . 7H_2O$ | 2.00 |
| $FeCl_3 . 6H_2O$ | 4.80 |
| $H_2SO_4$ | 3.00 ml |

The cell suspensions were treated with the edible protein additives at the conventional pH 4 and heated to 80° C. They were evaluated in a DeLaval Gyrotester, a small centrifuge specifically designed to measure centrifugation rate.

In the initial screening test 5 cc of the culture at pH 4 plus 1 cc of a 10% by wt. suspension of the flocculant in distilled water, plus 5 cc distilled water were used. Total volume of test solution was 11 cc. The samples were heated to 80° C., cooled and 10 cc of the samples centrifuged for 30 seconds.

The centrifuging operation was carried out in a calibrated tube in which the volume % of the fixed volume can be read directly. After the 30 second spin, two or three regions can be distinguished. The first region consists of densely packed solid in the bottom of the tube which will not decant when the supernatant liquid is poured out. This volume is recorded as dense pack in the table which follows. A second layer may form on top of the first consisting of relatively loosely packed material. This volume is recorded as loose pack in the table. The loosely packed material will decant. The remaining volume is the supernatant liquid which may contain undensified material. The volume of the supernatant liquid is given in the table and its appearance noted.

The higher the relative volume % of dense pack in the table, the better the flocculation. The relative values of dense pack to loose pack are indicative of the effectiveness of the separation in each case. The volume % values of the different flocculants are not directly comparable because the particle bulk or volume of each flocculant is different. Thus the volume of solids in 11 ml of the charge differs in each case.

Table I

| Protein Flocculant Added | Overall Rating | Settled Solids Dense Pack Vol. % | Settled Solids Loose Pack Vol. % | Super Natant Liquid Vol. % | Super Natant Liquid Appearance |
|---|---|---|---|---|---|
| Control (water only) | Very poor | 0.8 | 7.2 | 92 | Cloudy |
| Rice Flour | Poor | 1.1 | 9.9 | 89 | Cloudy |
| Casein | Fair | 3.0 | 5.0 | 92 | Cloudy |
| Gluten | Best | 10.0 | 0.0 | 90 | Clear |
| Skim Milk Powder | Best | 15.0 | 0.0 | 85 | Clear |
| Soy Bean Protein | Fair | 4.0 | 4.0 | 92 | Cloudy |
| Gelatin[A] | Best | 20.0 | 0.0 | 80 | Clear |
| Zein | Fair-Poor | 2.0 | 6.0 | 92 | Cloudy |

[A]Gelatin was not further tested because of its low food value and difficulty in handling the very viscous liquid.

The samples of skim milk and gluten were best but all materials tested showed some improvement over the control.

Additional tests were made with skim milk powder, gluten, casein and soy bean protein under varying conditions as shown in the tables below using only a 1% by weight suspension of the flocculants at pH 4.

The tests were conducted by taking a fixed volume of the bacterial culture, containing about 2.2 vol. % solids (cells). A fixed volume of water (control) or a 1% by wt. suspension of the flocculant was added to the culture. Thus the vol. % solids of the flocculant treated sample was higher than the control and was estimated at 3.0 vol. % solids. The test samples were centrifuged for 20 seconds, the supernatant liquid centrifuges until all the solid had been separated (1 minute). The vol. % of solids collected after the second centrifugation was measured, thus, in the table below 2.0 vol. % means that only 0.2 vol. % or about 9% of the original 2.2 vol. % solids of the culture sample had been removed in the initial 20 second centrifugation and that 91% of the original solids content remained and was precipitated only during the longer one minute cycle of centrifugation.

Table II

| 10 cc Bacterial Culture at Ambient Temperature Treated with: | Vol. % solids remaining after primary centrifugation | % solids removed in initial centrifugation |
|---|---|---|
| A 5 cc water (2.2 vol. % cells) (control) | 2.00 | 9.00 |
| B 5 cc:1% skim milk powder* | 0.01 | 99.97 |
| C 5 cc:1% gluten | 0.04 | 99.87 |
| D 5 cc:1% casein | 3.00 | Nil |
| E 5 cc:1% soy bean protein | 3.00 | Nil |

*0.8 vol. % added flocculant

Table II shows that skim milk powder and gluten were the most effective flocculants. Thus, under milder conditions of recovery, the heat sensitive components either in the cells or in the medium will not be affected. Casein and soy bean proteins apparently require a higher concentration to be effective since at the higher concentration in Table I (10% by wt.) these two protein supplements gave fair results but failed at the lower concentrations (1% by weight) as shown in Table II.

The above sequence was repeated but before the addition of the flocculants, the cell broth was first heated to 75° C. and cooled to room temperature. The results are shown below.

Table III

| 10 cc Bacterial Culture at ambient temperature treated with: | Vol. % solids remaining after primary centrifugation | % solids removed in initial centrifugation |
|---|---|---|
| A 5 cc water (2.2 vol % solids) (control) | 0.050 | 97.5 |
| B 5 cc: 1% skim milk powder[Z] | 0.030 | 99.0 |
| C 5 cc: 1% gluten | 0.030 | 99.0 |
| D 5 cc:1% casein | 0.038 | 98.7 |
| E 5 cc: 1% soy bean protein | 0.060 | 98.0 |

[Z]0.8 vol. % added flocculant

The above data show that heating the control in the conventional manner is effective in coagulating the cells and that the addition of a flocculant has only a slight beneficial effect. Heating has a deleterious effect on some of the nutrients in the cells and medium, as stated earlier.

In the next sequence, the flocculant was added first and the entire mixture was then heated to 75° C., cooled and centrifuged. The results are summarized below:

Table IV

| 10 cc Bacterial Culture at ambient temperature treated with: | Vol. % solids remaining after primary centrifugation | % solids removed in initial centrifugation |
|---|---|---|
| A 5 cc water (2.2 vol. % cells) (control) | 0.020 | 99.0 |
| B 5 cc: 1% skim milk powder* | 0.020 | 99.5 |
| C 5 cc: 1% gluten | 0.038 | 98.5 |
| D 5 cc: 1% casein | 0.050 | 98.4 |
| E 5 cc: 1% soy bean protein | 0.250 | 91.5 |

*0.8 vol. % added flocculant

While heating the cell medium was effective in raising the vol. % solids recovered with water only, it also shows that protein flocculants can be added to a treated cell broth which has been or is to be heated. Thus they can be used when required to complement the protein profile of the final product, even when not required for flocculation without detrimentally affecting the separation process, provided the heating of the cell broth is not objectionable.

Since skim milk and gluten performed best of the flocculants tested, the effect of pH by addition of $H_2SO_4$ was now investigated for these two substances. The results are summarized in the table below.

Effect of Edible Protein Additives on Microbial Cell Recovery By Centrifugation at Various pH Levels Vol. % Solids Remaining in Supernatant Liquid after 20 Seconds Centrifugation of 10 cc Bacterial Culture Cell Suspension Treated with 50 cc of 1% Solution of

| | Skim Milk Powder | Gluten | Water Control |
|---|---|---|---|
| pH 3.0 | 0.02 | 0.020 | 0.02 |

-continued

| Effect of Edible Protein Additives on Microbial Cell Recovery By Centrifugation at Various pH Levels | | | |
|---|---|---|---|
| | Vol. % Solids Remaining in Supernatant Liquid after 20 Seconds Centrifugation of 10 cc Bacterial Culture Cell Suspension Treated with 50 cc of 1% Solution of | | |
| | Skim Milk Powder | Gluten | Water Control |
| pH 4.0 | 0.01 | 0.015 | 1.25 |
| pH 4.5 | 0.06 | 0.040 | 3.80 |
| pH 5.0 | 5.00 | 0.400 | 5.00 |
| pH 6.0 | 5.00 | 6.000 | 9.00 |
| pH 6.5 | 10.00 | 10.000 | 10.00 |

The results show that the addition of these flocculants is effective at a range of pH 4–pH 6 and that at pH 4–4.5, the recovery is better than for water at a pH of 4. At pH 5, gluten was definitely a superior flocculant; skimmed milk powder became more effective at the slightly lower pH 4–4.5. At pH 3 the sample changes to a light yellow color, indicating some product deterioration. By operating at a higher pH less acid hydrolysis of the amino acids will take place. There is a decided advantage in being able to recover product at ambient temperature and higher pH (nearer pH 6) so that hydrolysis and cell breakdown are inhibited. Once the cells have been separated from the medium, the cells can be heat treated if desired, for example during the final drying step or they can be sterilized by irradiation.

The effect of concentration of flocculation efficiency was studied on skim milk powder. A 1% by weight solution was made up and added as shown below to 10 cc of culture at pH 4 at ambient temperature. The results are tabulated below.

| Effect of Various Concentrations of Skim Milk Powder on Microbial Cell Recovery by Centrifugation | | |
|---|---|---|
| | 10 cc Bacterial Culture Treated with | % Solids Remaining in Supernatant Liquid After 20 Seconds Centrifugation |
| 1 | 2.5 cc water | 1.50 |
| 2 | 0.2 cc 1% skim milk powder suspension + 2.3 cc water | 0.50 |
| 3 | 0.5 cc 1% skim milk powder suspension + 2.0 cc water | 0.30 |
| 4 | 1.0 cc 1% skim milk powder suspension + 1.5 cc water | 0.05 |
| 5 | 1.5 cc 1% skim milk powder suspension + 1.0 cc water | 0.03 |
| 6 | 2.0 cc 1% skim milk powder suspension + 0.5 cc water | 0.03 |
| 7 | 2.5 cc 1% skim milk powder | 0.02 |

The activity of skim milk as a flocculant was quite high and as little as 0.8 g/liter of skim milk powder may be used (line 4 of above table). However, as pointed out above, larger quantities may be desirable from a nutritional point of view. Since all the protein supplement flocculants were better than the control the selection of the flocculant(s) can be made either on the basis of desired nutritive balance or on the basis of most desirable operation conditions. Adjustments can be made as necessary. For example soy bean protein, including a heating step; a higher concentration of soy bean protein at ambient temperature, or a combination of, for example, soy bean protein and gluten can be used.

Illustrative of the concept of using both an effective flocculant, and a less effective or poor flocculant in combination with a cell recovery step is given below:

For example, an amino acid profile of wheat flour and rice flour is given below, together with the amino acid profile given earlier, on the basis of g of amino acid/100 g protein.

| Essential Amino Acid Content (g amino acid/100g protein) | | | | | | |
|---|---|---|---|---|---|---|
| | Flocculant | | Non-Flocculant | | | |
| Essential Amino Acid | Skimmed Milk Powder | Gluten | Wheat Flour | Rice Flour | Single Cell Protein Bacterial | Single Cell Protein Yeast |
| Leucine | 10.63 | 7.16 | 5.22 | 6.38 | 7.30 | 8.13 |
| Isoleucine | 5.50 | 3.48 | 3.60 | 4.00 | 3.96 | 5.22 |
| Lysine | 8.10 | 1.67 | 3.18 | 3.15 | 5.22 | 7.31 |
| Methionine | 2.01 | 1.50 | 1.27 | 1.75 | 1.67 | 1.24 |
| Cystine | 0.26 | 1.35 | 1.67 | 1.13 | 0.40 | 0.85 |
| Threonine | 3.80 | 2.05 | 2.35 | 3.25 | 3.59 | 5.51 |
| Phenylalanine | 5.60 | 4.72 | 4.25 | 3.88 | 3.10 | 5.31 |
| Tyrosine | 4.80 | 3.48 | 3.20 | 7.52 | 3.51 | 4.80 |
| Tryptophane | —[1] | — | 1.40 | 1.25 | 0.66 | 2.00 |
| Valine | 6.80 | 3.61 | 3.45 | 5.38 | 5.09 | 6.25 |

[1]Tryptophane was not analyzed for in these flocculants.

In the above table, for example, cystine, an essential amino acid is present at a much higher level in wheat flour, a poor flocculant, than in the flocculants or the single cell proteins. Thus, a combination of skimmed milk powder and bacterial single cell protein would be benefitted by the addition of wheat flour to provide more cystine without sacrificing the essential presence of an effective flocculant. The resulting dry solids, recovered from this operation is an effective proteinaceous food.

Reasonable variation and modification are possible within the scope of the foregoing disclosure and the appended claims to the invention the essence of which is that a material suitable as a food is used as a flocculant in the recovery of cellular protein products from microbiologically produced masses.

I claim:

[1. In the process of recovering microbiologically produced cellular protein products useful as animal food from the medium in which they were produced by adjusting the pH to a level which will permit flocculation, adding a sufficient amount of a flocculating agent to cause flocculation, followed by physical separation, the improvement comprising utilizing as the flocculating agent a proteinaceous material capable of flocculating the cellular protein products.]

[2. The process according to claim 1 wherein the proteinaceous material is at least one of casein, gluten, skim milk powder, soy bean protein, gelatin, or zein.]

[3. The process according to claim 2 wherein the amount and the type of proteinaceous flocculating agent used are such as to obtain a recovered product containing a balanced mixture of amino acids.]

[4. The process according to claim 2 wherein the amount of proteinaceous flocculant employed in the recovery process is in the approximate range of from about 0.2 to about 25 weight percent of the total weight of the cells and growth medium.]

[5. The process according to claim 1 wherein the cells and the growth medium are at ambient temperature during the recovery process.]

[6. The process according to claim 5 wherein the pH of the cells and growth medium to which the flocculant is added is in the range of about 4to about 6.]

[7. The process according to claim 6 wherein the proteinaceous material is casein.]

[8. The process according to claim 6 wherein the proteinaceous material is skim milk powder.]

[9. The method of recovering microbiologically produced cells at ambient temperature from the medium in which they were produced comprising adding to the medium a proteinaceous material capable of flocculating the cells in an amount sufficient to cause flocculation, said amount being at least about 0.2 weight percent based on the total weight of the cells and growth medium, and adjusting the pH to a level in the range of about 4 to about 6 that will permit flocculation, and then physically separating the flocculated cells and the growth medium.]

*10. A process of recovering microbiologically produced cells from the medium in which they were produced comprising adding to the cell-containing medium gluten in an amount sufficient to cause flocculation at a pH in the range of 4 to 6, said addition of said gluten being made when said cell-containing medium is at a pH in the range of 4 to 6 that will permit flocculation, and then physically separating the flocculated cells from the medium in which they were produced.*

*11. A process according to claim 10 wherein the amount of said gluten is at least equal to about 0.2 percent of the total weight of the cells and the growth medium.*

*12. In the process of recovering microbiologically produced cellular protein products useful as animal food from the medium in which they were produced by adjusting the pH to a level in the range of 4 to 6 which will permit flocculation, adding a sufficient amount of a flocculating agent to cause flocculation, followed by physical separation, the improvement comprising utilizing gluten as the flocculating agent.*

*13. The process according to claim 12 wherein the amount of gluten employed in the recovery process is in the approximate range of from about 0.2 to about 25 weight percent of the total weight of the cells and growth medium.*

*14. The process according to claim 13 wherein the cells and the growth medium are at ambient temperature during the recovery process.*

*15. A process according to claim 13 wherein the flocculation is effected at a pH in the range of about 4 to about 5.*

*16. A process according to claim 15 wherein the flocculation is effected at a pH of about 5.*

*17. The method of recovering microbiologically produced cells at ambient temperature from the medium in which they were produced comprising adding to the medium gluten in an amount sufficient to cause flocculation at a pH in the range of 4 to 6, said amount being at least about 0.2 weight percent based on the total weight of the cells and growth medium, and adjusting the pH to a level in the range of 4 to 6 that will permit flocculation, and then physically separating the flocculated cells from the growth medium.*

* * * * *